United States Patent [19]

Chibnik

[11] 4,212,754

[45] Jul. 15, 1980

[54] CHELATE DETERGENT AND ANTIWEAR ADDITIVE FOR LUBRICANTS DERIVED FROM HYDROXYALKYLATED BENZOTRIAZOLES

[75] Inventor: Sheldon Chibnik, Cherry Hill, N.J.

[73] Assignee: Mobil Oil Corporation, New York, N.Y.

[21] Appl. No.: 32,079

[22] Filed: Apr. 23, 1979

[51] Int. Cl.² ............................................. C10M 1/10
[52] U.S. Cl. ..................... 252/49.7; 44/63; 44/68; 260/429 J; 548/104; 548/113; 548/260; 260/326.22
[58] Field of Search ............... 252/49.7, 51.5 A; 44/63, 68; 260/308 B, 429 J

[56] References Cited

U.S. PATENT DOCUMENTS

| | | | |
|---|---|---|---|
| 2,628,942 | 2/1953 | Morris et al. | 252/49.7 |
| 3,652,616 | 3/1972 | Watson et al. | 252/49.7 X |
| 3,884,932 | 5/1975 | Andress, Jr. | 260/308 B |
| 3,897,351 | 7/1975 | Davis et al. | 260/308 B X |
| 3,945,933 | 3/1976 | Chibnik et al. | 44/63 X |
| 4,011,167 | 3/1977 | Chibnik et al. | 252/49.7 X |
| 4,035,309 | 7/1977 | Brois | 252/49.7 |
| 4,093,614 | 6/1978 | Chibnik et al. | 44/63 X |
| 4,144,180 | 3/1979 | Andress, Jr. | 260/308 B X |
| 4,153,564 | 5/1979 | Chibnik | 260/308 B X |

*Primary Examiner*—Andrew Metz
*Attorney, Agent, or Firm*—Charles A. Huggett; Hastings S. Trigg

[57] ABSTRACT

There are provided complexes of metal salts prepared by (1) reacting a benzotriazole with a monoepoxide to form a hydroxyalkylbenzotriazole, (2) reacting the hydroxyalkylbenzotriazole with an alkenylsuccinic anhydride to form a monoester, and (3) converting the monoester to the salt of a metal which can form Werner complexes and complexing with a ligand containing amine, hydroxyl, oxazoline, or imidazoline groups to form a chelate. These chelates impart detergent and antiwear properties to lubricants.

12 Claims, No Drawings

CHELATE DETERGENT AND ANTIWEAR ADDITIVE FOR LUBRICANTS DERIVED FROM HYDROXYALKYLATED BENZOTRIAZOLES

FIELD OF THE INVENTION

This invention is concerned with Werner complexes of novel metal salts with compounds capable of forming Werner complexes.

BACKGROUND OF THE INVENTION

Certain coordinate metal complexes have been proposed as additives to improve detergency properties of fuels and lubricants. For example, succinimides have been complexed with metal phenates (U.S. Pat. No. 4,011,167); simple salts (U.S. Pat. Nos. 3,306,908 and 3,652,616); and sulfonate, phosphate, phosphinate, phosphonate, and sulfamate salts (U.S. Pat. Nos. 3,642,847 and 3,649,661). Insofar as is now known the salts described in this specification have not been complexed to form Werner coordination complexes. Further, it is a discovery of this invention that such complexes not only improve detergency characteristic but also antiwear properties of lubricants.

SUMMARY OF THE INVENTION

This invention provides Werner coordination complexes prepared by (1) reacting a benzotriazole with a monoepoxide to form a mixture of 1-and 2-hydroxyalkylbenzotraizoles, (2) esterifying said mixture or one of the isomers thereof with alkenylsuccinic anhydride to form a monoester, (3) converting said monoester to a salt of a metal selected from Groups I B, II B, IV B, and VIII of the Periodic Table, and (4) complexing it with a ligand containing amine, hydroxyl, oxazoline, or imidazoline groups to form a chelate.

It also provides a composition comprising a major proportion of a lubricating oil or a hydrocarbon fuel and an amount sufficient to impart detergency properties thereto of such chelate.

DESCRIPTION OF SPECIFIC EMBODIMENTS

The following reaction sequence is illustrative of the preparation of the Werner coordination metal complexes of this invention:

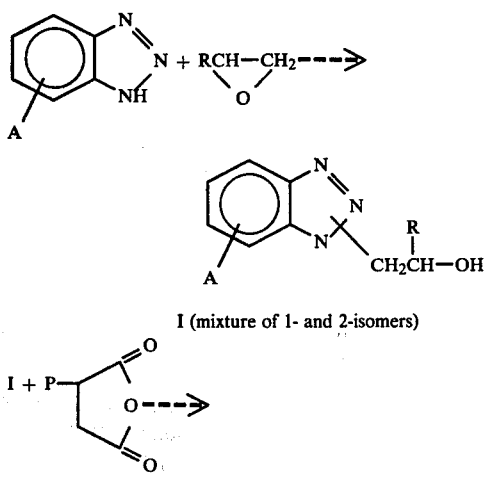

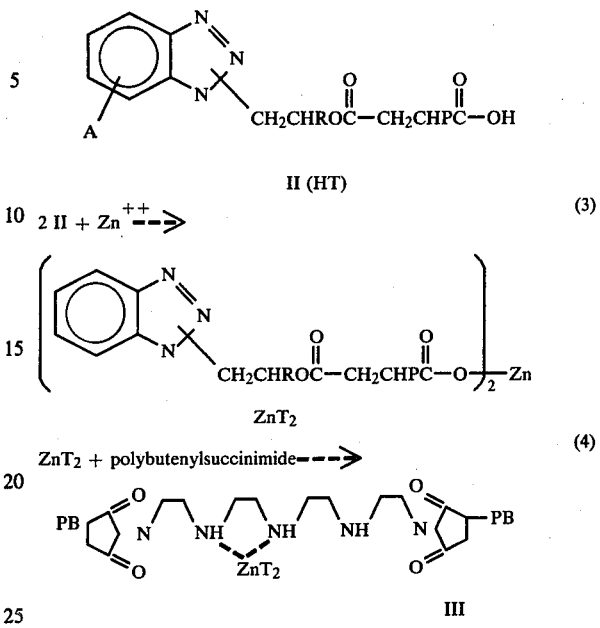

In preparing the Werner complexes of this invention, the benzotriazole reactant is benzotriazole (azimidobenzene) or a lower alkylbenzotriazole, such as methylbenzotriazole (azimidotoluene or toluoltriazole).

The monoepoxide reactant can be a 1,2-epoxy compound having the formula

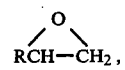

wherein R is hydrogen or an alkyl radical having between 1 and 30 carbon atoms, or it can be an internal oxirane or an epoxidized ring. Such compounds include ethylene oxide (oxirane); propylene oxide (2-methyloxirane); butyl glycidylether; 2,3-epoxyoctane; 2,3-epoxydecane, styrene oxide; cresyl glycidyl ether; epoxidized natural oils; such as soybean oil; epoxycyclohexane; and epoxidized mixtures of $C_{10}$–$C_{28}$ alpha-olefins. A wide variety of monoepoxides are available commercially.

The reaction between the benzotriazole and monoepoxide in Step (1) is preferably carried out in a suitable solvent which (1) is not reactive to epoxides under usual reaction conditions, (2) preferably is a solvent for the benzotriazole reactant, and (3) is easily removed. Typical solvents include t-butanol, benzene, toluene, xylene, and halogenated hydrocarbons. In general, the reaction is carried out at a temperature between about 25° C. and , about 200° C. for between about 1 hour and about 24 hours.

As indicated in the Step (1) equation, the hydroxyalkylbenzotriazole is formed as a mixture of 1-and 2-isomers. These isomers occur in a weight ratio of about 3:1, which can be readily separated by distillation. It is within the contemplation of this invention to use either the mixture of isomers or one of the isomers alone in making the complexes of this invention. Further the reaction product of Step (1) may contain minor amounts of by-products impurities. These may be removed, as by distillation, if desired. For the purposes of this invention, however, such removal is not necessary.

In Step (2), the hydroxyl group of the hydroxalkylbenzotriazole(s) is esterified with an alkenylsuccinic anhydride. The alkenylsuccinic anhydrides are well known and are available commercially. They are prepared by known techniques from an olefin or polyolefin and maleic anhydride. The preferred alkenylsuccinic anhydride will contain between about 30 carbon atoms and about 170 carbon atoms in the alkenyl group, but in general can contain between about 2 carbon atoms and about 200 carbon atoms per alkenyl group. The olefin used to prepare the alkenylsuccinic anhydride can be a simple 1-alkene, such as 1-octene, 1-decene, 1-dodecene, etc., or it can be a polymer or copolymer of such olefins as ethylene, propylene, 1-butene, isobutene, 1-pentene, 1-hexene, 1-decene, and so forth.

The reaction between the hydroxyalkylbenzotriazole and alkenylsuccinic anhydride is carried out under mild conditions to form a monoester, leaving a free carboxyl group. Generally, the reaction is carried out at a temperature between about 40° C., and about 130° C. for between about 0.5 hour and about 8 hours.

The resulting acid ester of the hydroxyalkylbenzotriazole is neutralized with a polyvalent metal, especially divalent metals, using known techniques of salt formation. The metal is selected from Groups IB, IIB, IVA, VIB, and VIII of the Periodic Table. The acceptable metals include zinc, tin, nickel, copper, cobalt, cadmium, chromium, and lead. Of these, the most preferred are zinc and nickel.

The metal salts produced as described hereinbefore are reacted with a ligand to form a coordinated complex or chelate. The preferable ligands are compounds containing at least two amine, hydroxyl, oxazoline, or imidazoline groups which have the capability to complex metal salts to form chelates. Such compounds are known to those skilled in the art.

One type of ligand is a polyalkylene polyamine having the formula $H_2N(RNH)_xH$, wherein R is an alkylene group having 2-5 carbon atoms and x is 1-10. Nonlimiting examples of such compounds are triethylenetetramine, tetraethylenepentamine, di(methylethylene) triamine, and hexapropyleneheptamine.

As is disclosed in U.S. Pat. No. 3,624,115 to which reference is made, the polyalkylenepolyamine can be reacted with a monocaboxylic acid of 1-40 carbon atoms (forming an amide or imidazoline) and with an alkenylsuccinic acid or anhydride having 8-300 carbon atoms in the alkenyl group (forming a succinimide).

As is disclosed in U.S. Pat. No. 4,011,167, to which reference is made, the ligand can be formed from polyalkylene polyamine and alkenylsuccinic anhydride. In accordance with U.S. Pat. No. 3,649,661, to which reference is made, the ligand can be formed in any desired order, i.e., the polyalkylene polyamine can be reacted with the polyalkenylsuccinic anhydride before chelate formation or it can be reacted with a metal salt to form a chelate followed by reaction with an alkenylsuccinic anhydride. Other acid or aldehyde derivatives of polyalkylene polyamines, i.e., succinimide-amindes, succinimide-imidazolines, and succinimide-imidazolidines are disclosed in U.S. Pat. No. 3,445,386, to which reference is made, and are utilized as ligands.

Other utilizable ligands are described in commonly-assigned copending application Ser. No. 727,197, filed Sept. 27, 1976 and now abandoned, to which reference is made. These ligands are prepared by reacting alkenylsuccinic anhydride or acid with an amino alcohol or a polyhydric alcohol and have the formula:

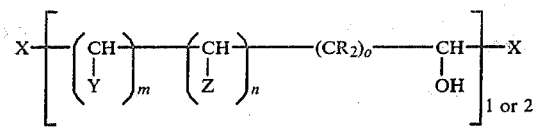

wherein m, n and o are zero or 1, X is hydrogen or a group containing a hydrocarbon having greater than 30 carbon atoms, preferably from 50 to 300 carbon atoms, R is selected from the group consisting of hydrogen, hydroxyl, hydroxymethyl, amino and a hydrocarbyl of from 1 to 15 carbon atoms, Y and Z are OH or N<, wherein the N< is an amino group containing hydrogen, alkyl or a mixture thereof or is part of a ring system containing from 4 to 5 carbon atoms, wherein the rings has thereon a polyalkyl group containing greater than 30 carbon atoms, preferably 50 to 300 carbon atoms.

Preferred among the compounds contemplated are the products obtained by reacting polyalkylsuccinic acid derivatives with an amino alcohol or polyhydric alcohol of the formula:

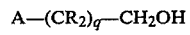

wherein R is hydrogen, alkyl of 1 to 15 carbon atoms, hydroxyl, amino or $CH_2OH$, A is $NH_2$ or $CH_2OH$, q is 1 or 2 when A is $NH_2$ or q is 0 or 1 when A is $CH_2OH$.

Depending upon which reactants are used and the reaction conditions, these compounds are diesters, imides, oxazolines, imidazolines, or amides, as is fully described in Ser. No. 727,197.

Step (4) is the formation of the chelate (coordination metal complex) by reacting the aforedescribed polyvalent metal salt with a ligand. This step is carried out at temperatures between about 50° C. and about 180° C., for between about 0.1 hour and about 2 hours. Steps (2), (3), and (4) are usually carried out in a light process oil, such as Promor oil, a refinery process oil produced by the furfural extraction of a high paraffin feed stream. It has low aromatic and naphthenic contents and has a sulfur content of about 0.5 weight percent. Its viscosity is such that it is suitable as a solvent in certain commercial operations.

The following examples demonstrate the preparation of the chelates of this invention and their use in mineral oils.

EXAMPLE 1

Preparation of Hydroxypropylbenzotriazoles

A one-gallon autoclave was charged with 450 g. benzotriazole, 1415 g. t-butanol and 227 g. propylene oxide. The autoclave was heated to 150° C. and stirred at that temperature for 20 hours. The vessel was cooled, vented and the product stripped of solvent and a small amount of starting materials by heating to 145° C. at 1 Torr. The product yield was 97% comprised of 1.7% 1-methylbenzotriazole, 9.3% of two unidentified materials and 89% hydroxypropylbenzotriazoles (mixed 1- and 2-isomers). The two isomers occur in about a 3/1 ratio and can be readily separated by distillation if desired.

Esterification and Formation of a Zinc Salt $ZnT_2$

A polybutenylsuccinic anhydride was prepared via known methods from 500 molecular weight polybutene and maleic anhydride. The material contained 22% unreacted polybutene which was not separated. This PBSA (262 g.) was heated together with 73 g. of the crude product described above and 218 g. of Promor oil at 150° C. for 2 hours. An infrared spectrogram showed both ester and acid groups. The acid value was 41.8 (calc'd. for monoester 35.9). The mixture was cooled to 90° C. and a slurry of 15 g. zinc oxide in 55 g. water was added. These conditions were held for 2 hours, after which the water was stripped to a final pot temperature of 150° C. at 2 Torr.

Formation of Chelate

A polybutenyl succinimide was prepared from two moles of 1300 MW polybutenylsuccinic anhydride and one mole of tetraethylenepentamine. This material (900 g.) and 300 g. Promor oil were added to the $ZnT_2$ prepared above and reacted at 100° C. for one hour. The complex was diluted with 1341 g. Promor oil and filtered. The zinc content was 0.21% (calc'd. 0.38).

EXAMPLE 2

Example 1 was repeated, with the exception that the 1-isomer of hydroxypropylbenzotriazole was isolated and used on a mole for mole basis instead of the mixed isomers.

EXAMPLE 3

Example 1 was repeated, with the exception that the 2-isomer of hydroxypropylbenzotriazole was isolated and used on a mole for mole basis instead of the mixed isomers.

EXAMPLE 4

Example 1 was repeated on a mole for mole basis, with the exception that mixed isomers of hydroxypropyltoluoltriazoles were used.

EXAMPLE 5

Example 1 was repeated, with the exception that dodecenylsuccinic anhydride was used on a mole for mole basis in the esterification step instead of the 500 MW polybutenylsuccinic anhydride.

EXAMPLE 6

A polybutenylsuccinic anhydride was prepared from 1300 molecular weight (M.W.) polybutene and maleic anhydride and was then reacted with hydroxypropylbenzotriazoles (mixed isomers) to form the monoester as described in Example 1. Then as described in Example 1, the monoester was converted to the zinc salt.

EXAMPLE 7

An oil soluble oxazoline was prepared by reacting one mole of polybutenyl (1300 M.W.) succinic anhydride with one mole of 2-amino-2-ethyl-1,3-propanediol. A chelate was prepared, as described in Example 1, using one molar equivalent of zinc contained in the zinc salt of Example 6 per molar equivalent of aminoethylpropanediol.

EXAMPLE 8

A Mannich base was prepared via known methods from 900 M.W. polybutylphenol, formaldehyde, and diethylenetriamine. A 1:1 molar chelate was formed with the zinc salt of Example 6 as described in Example 1.

EXAMPLE 9

A hydroxy ester was prepared from one mole of polybutenyl (1300 M.W.) succinic anhydride and one mole of pentaerythritol. This was chelated (1:1 mole) with the zinc salt of Example 6 as described in Example 1.

The additives of this invention can be used in any one of the wide variety of oils of lubricating viscosity, such as natural, refined or synthetic oils, in blends of such oils, or in greases made therefrom. These oils may be prepared within or without auxiliary conventional additives such as: oiliness and extreme pressure agents; corrosion, oxidation and rust inhibitors; viscosity index improving agents; coloring agents and auxiliary detergents. The useful oils include mineral oils, both naphthenic and paraffinic, either or both containing aromatic fractions. They include, among the synthetic oils, the synthetic hydrocarbon oils as well as synthetic ester oils prepared from, for example, monohydric alcohols and polyfunctional acids or from the polyhydric alcohols and monofunctional acids. In this latter category are esters prepared from pentaerythritol and $C_5$ aliphatic mono acid such as valeric acid or from such alcohol and a mixture of $C_5$-$C_9$ aliphatic monofunctional acids.

The fuels contemplated are liquid hydrocarbon combustion fuels, including the distillate fuels, i.e., gasoline and fuel oils. Accordingly, the fuel oils that may be improved in accordance with the present invention are hydrocarbon fractions having an initial boiling point of at least about 100° F. and an end-boiling point no higher than about 750° F. and boiling substantially continuously throughout their distillation range. These fuel oils are generally known as distillate fuel oils.

It is to be understood, however, that this term is not restricted to straight run distillate factions. The distillate fuel oils can be straight run or distillate fuel oils, catalytically or thermally cracked (including hydrocracked) distillate fuel oils, or mixtures of straight run distillate fuel oils, naphthas and the like, with cracked distillate stocks. Moreover, such fuel oils can be treated in accordance with well-known commercial methods, including acid or caustic treatment, hydrogenation, solvent refining, clay treatment and the like.

The distillate fuel oils are characterized by their relatively low viscosities, pour points, and similar properties. The principal property which characterizes the contemplated hydrocarbons, however, is the distillation range. As mentioned hereinbefore, this range lies between about 100° F. and about 750° F. Obviously, the distillation range of each individual fuel oil will cover a narrower boiling range, but falling, nevertheless, within the above-specified limits. Likewise, each fuel oil will boil substantially continuously throughout its distillation range.

Contemplated among the fuel oils are Nos. 1, 2 and 3 fuel oils (useful in heating and in diesel engines) and the jet combustion fuels. The domestic fuel oils generally conform to the specifications set forth in A.S.T.M. Specifications D396-48T. Specifications for diesel fuels are defined in A.S.T.M. Specification D975-48%. Typical jet fuels are defined in Military Specification MIL-F-5624B.

The gasolines that are improved by the additive compositions of this invention are mixtures of hydrocarbons having an initial boiling point falling between about 75° F. and about 135° F. and an end-boiling point falling between about 250° F. and about 450° F. As is well-known in the art, motor gasoline can be straight run gasoline or, as is more usual, it can be a blend of two or more cuts of materials including straight run stock, catalytic or thermal reformate, cracked stock alkylated natural gasoline and aromatic hydrocarbons. All these are contemplated.

The amount of chelate of this invention that is added to a lubricating oil or a hydrocarbon fuel is a minor amount sufficient to impart detergency properties thereto. In general, the amount used can be between about 0.05 percent and about 2.5 percent by weight thereof.

EVALUATION OF THE COMPOUNDS

The compounds of this invention were evaluated in the following tests:

Diesel Oil Test (DOT)

This test was developed to produce deposits from the oxidation of lubricating oil under conditions which closely approximate those found in the piston zone of a diesel engine. The test comprises an aluminum cylinder heated by radiation from an external source. The surface temperature of the cylinder is maintained at 575° F. during the 140-minute test period. The shaft turns slowly (2 RPM) and dips into an oil sump where it picks up a thin film of oil. This thin film is carried into the oxidation zone where heated gases (moist air at 350° F. is typically employed, but nitrogen oxides, sulfur oxides and the like may be used) form oxidation deposits. These deposits can be affected by the detergent as the test cylinder rotates into the sump. The efficiency of the detergent is rated by the color and intensity of the deposits on the shaft at the end of the test.

Specifically, 20 parts of each chelate (on a non-oil basis) was compounded with 947 parts of a solvent refined SAE 30 grade lubricating oil, 16 parts of calcium sulfonate, 4 parts of calcium phenate, 10 parts of zinc organodithiophosphate and 1 part of an acrylic ester polymer VI improver. Parts are by weight.

The results are as follows. In the test, 100 is clean. Without detergent, the rating is <50.

| Example | Rating |
| --- | --- |
| 2 | 68 |
| 3 | 67 |
| 4 | 73 |
| 5 | 70 |
| 7 | 81 |
| 8 | 70 |
| 9 | 74 |

Antiwear Test

The chelates (0.53 wt.%, non-oil basis) were each dissolved in 150 second solvent refined paraffinic bright stock and tested in the Shell 4-ball wear machine at 200° F., using a 200 kg. load, for one hour at 1800 RPM. Results were as follows. A smaller scar shows improvement in antiwear properties.

| Example | Scar Diameter, mm. |
| --- | --- |
| Base oil | 0.70 |
| 2 | 0.47 |
| 3 | 0.47 |
| 5 | 0.33 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. Chelates prepared by (1) reacting in a 1:1 molar ratio a benzotriazole reactant with a monoepoxide at a temperature between about 25° C. and about 200° C. for between about one hour and about 24 hours to form a mixture of 1- and 2-hydroxyalkylbenzotriazoles, (2) esterifying said mixture or one of the isomers thereof with alkenylsuccinic anhydride at a temperature between about 40° C. and about 130° C. for between about 0.5 hours and about 8 hours to form a monoester, (3) converting said monoester to a salt of a metal selected from Groups IB, IIB, IVB, and VII of the Periodic Table, and (4) complexing said salt with a ligand containing amine, hydroxyl, oxazoline, or imidazoline groups to form a chelate.

2. A chelate of claim 1, wherein said benzotriazole reactant is benzotriazole, said monoepoxide is propylene oxide, said hydroxyalkylbenzotriazole is hydroxypropylbenzotriazole, said alkenylsuccinic anhydride is polybutenylsuccinic anhydride in which the polybutene has a molecular weight of about 500, said metal is zinc, and ligand is a polybutenylsuccinimide prepared from two moles 1300 molecular weight polybutenylsuccinic anhydride and one mole tetraethylenepentamine.

3. A chelate of claim 2, wherein the isomer is 1-hydroxypropylbenzotriazole.

4. A chelate of claim 2, wherein the isomer is 2-hydroxypropylbenzotriazole.

5. A chelate of claim 2, wherein said benzotriazole reactant is tolyltriazole and said hydroxypropylbenzotriazole is hydroxypropyltolyltriazole.

6. A chelate of claim 2, wherein said esterifying alkenylsuccinic anhydride is dodecenylsuccinic anhydride.

7. A composition comprising a major proportion of a lubricating oil or a hydrocarbon fuel and an amount sufficient to impart detergency properties thereto of a chelate of claim 1.

8. A composition comprising a major proportion of a lubricating oil or a hydrocarbon fuel and an amount sufficient to impart detergency properties thereto of a chelate of claim 2.

9. A composition comprising a major proportion of a lubricating oil or a hydrocarbon fuel and an amount sufficient to impart detergency properties thereto of a chelate of claim 3.

10. A composition comprising a major proportion of a lubricating oil or a hydrocarbon fuel and an amount sufficient to impart detergency properties thereto of a chelate of claim 4.

11. A composition comprising a major proportion of a lubricating oil or a hydrocarbon fuel and an amount sufficient to impart detergency properties thereto of a chelate of claim 5.

12. A composition comprising a major proportion of a lubricating oil or a hydrocarbon fuel and an amount sufficient to impart detergency properties thereto of a chelate of claim 6.

* * * * *